US012514747B1

(12) United States Patent
Yang

(10) Patent No.: US 12,514,747 B1
(45) Date of Patent: Jan. 6, 2026

(54) NECK FAN

(71) Applicant: Xiang Yu Yang, Guangdong (CN)

(72) Inventor: Xiang Yu Yang, Guangdong (CN)

( * ) Notice: Subject to any disclaimer, the term of this patent is extended or adjusted under 35 U.S.C. 154(b) by 0 days.

(21) Appl. No.: 19/051,875

(22) Filed: Feb. 12, 2025

(30) Foreign Application Priority Data

Dec. 17, 2023 (CN) ......................... 202323448940.0

(51) Int. Cl.
*A61F 7/00* (2006.01)

(52) U.S. Cl.
CPC ..... *A61F 7/0085* (2013.01); *A61F 2007/0011* (2013.01); *A61F 2007/0064* (2013.01)

(58) Field of Classification Search
CPC ............ A61F 7/0085; A61F 2007/0011; A61F 2007/0064; A61F 2007/0067; A61F 2007/0059; A61F 2007/006; A61F 2007/0063; A61F 7/00; A61F 7/02; F04D 25/166; F04D 29/4213; F04D 29/424; F04D 29/4246; F04D 25/0673; F04D 29/005; F04D 25/084
See application file for complete search history.

(56) References Cited

U.S. PATENT DOCUMENTS

| | | | | |
|---|---|---|---|---|
| 7,484,925 | B2 * | 2/2009 | Carlson | F04D 29/384 416/244 R |
| 11,187,241 | B1 * | 11/2021 | Liu | F04D 29/441 |
| 11,624,370 | B2 | 4/2023 | Liu et al. | |
| 11,754,080 | B2 | 9/2023 | Jiahang et al. | |
| 11,920,602 | B2 | 3/2024 | Li | |
| 12,060,893 | B2 | 8/2024 | Liu et al. | |
| 12,188,481 | B1 | 1/2025 | Li | |
| 2005/0260070 | A1 * | 11/2005 | Hsu | F04D 25/0606 415/199.6 |
| 2022/0333606 | A1 * | 10/2022 | Xie | F04D 25/084 |
| 2023/0332620 | A1 | 10/2023 | Dong et al. | |
| 2025/0012286 | A1 | 1/2025 | Xie et al. | |

FOREIGN PATENT DOCUMENTS

| | | | |
|---|---|---|---|
| CN | 211116731 | U | 7/2020 |
| CN | 211648548 | U | 10/2020 |
| CN | 214404035 | U | 10/2021 |
| CN | 214404036 | U | 10/2021 |
| CN | 117167319 | A | 12/2023 |
| CN | 220452282 | U | 2/2024 |

* cited by examiner

*Primary Examiner* — Adam Z Minchella
*Assistant Examiner* — Ashleigh Lauren Kern
(74) *Attorney, Agent, or Firm* — HOWARD M COHN and Associates, LLC

(57) ABSTRACT

The neck fan includes a neck fan main body and fan blade groups. The neck fan main body includes a blowing housing. The blowing housing forms an accommodating cavity, an air inlet and an air outlet. The fan blade groups arranged in the accommodating cavities. Each fan blade group includes a base plate, a first centrifugal vane wheel, and a second centrifugal vane wheel. The second centrifugal vane wheel is arranged around a periphery of the first centrifugal vane wheel. Each blowing housing includes a first side, a second side opposite to the first side, a third side and a fourth side. The at least one air inlet is provided in one of the first side and the second side and the other one of the first side and the second side has no air inlet, so that the blowing housing is formed into a single-sided air inlet structure.

20 Claims, 10 Drawing Sheets

NECK FAN

CROSS-REFERENCE TO RELATED APPLICATIONS

The application claims priority of Chinese patent application CN202323448940.0, filed on Dec. 17, 2023, which is incorporated herein by reference in its entireties.

TECHNICAL FIELD

The present disclosure relates to the technical field of fans, and in particular, to a neck fan.

BACKGROUND

As is well known, a neck fan is hung around a neck. Fan blade groups for blowing air are provided at two ends of a housing of the neck fan, to cool a user. However, in the existing neck fan, air inlets are provided in the housing and on two sides of the fan blade groups to increase an air intake volume. This can cause the hairs of a user to easily wrap around the air inlets, leading to fan failure or user injury. In addition, supplying air from both sides can also make it easier for dust and impurities to enter the product, which easily causes a product failure. Secondly, circuit boards and batteries are further arranged inside the housing. Some batteries and circuit boards are scattered inside the housing, so when rainwater or sweat falls into the housing through gaps such as the air inlets or air outlets, the circuit boards and batteries may get wet, causing product failure and affecting use of the product.

SUMMARY

To solve the problem of a product failure easily caused by a neck fan in which air is supplied from both sides, the present disclosure provides a neck fan.

In the first aspect, The present invention provides a neck fan.

A neck fan configured to be worn around the neck of a user. The neck fan includes a neck fan main body and fan blade groups.

The neck fan main body includes two blowing main bodies respectively configured to be arranged on two sides of the neck of the user, each blowing main body includes a blowing housing; the blowing housing forms an accommodating cavity and is provided with at least one air inlet communicated to the accommodating cavity and at least one first air outlet communicated to the accommodating cavity.

The fan blade groups arranged in the accommodating cavities. Each fan blade group includes a base plate, a first centrifugal vane wheel, and a second centrifugal vane wheel; the first centrifugal vane wheel and the second centrifugal vane wheel are arranged on the same side of the base plate, and the second centrifugal vane wheel is arranged around a periphery of the first centrifugal vane wheel; each blowing housing includes a first side, a second side opposite to the first side, a third side adjacent to the first side and the second side, and a fourth side adjacent to the third side; the at least one air inlet is provided in one of the first side and the second side, and corresponds to the first centrifugal vane wheel and the second centrifugal vane wheel; the other one of the first side and the second side has no air inlet, so that the blowing housing is formed into a single-sided air inlet structure; and the first centrifugal vane wheel and the second centrifugal vane wheel are configured to guide air from the air inlet on a single side to the at least one first air outlet for blowing out.

In the second aspect, The present invention also provides a neck fan. The neck fan includes a neck fan main body and fan blade groups.

The neck fan main body includes two blowing main bodies respectively configured to be arranged on two sides of the neck of the user. Each blowing main body includes a blowing housing; the blowing housing forms an accommodating cavity and is provided with at least one air inlet communicated to the accommodating cavity and at least one first air outlet communicated to the accommodating cavity.

The fan blade groups arranged in the accommodating cavities of the blowing housings;

each blowing housing includes a first side and a second side opposite to the first side; the at least one air inlet is provided in one of the first side and the second side, and corresponds to the fan blade group; the other one of the first side and the second side has no air inlet, so that the blowing housing is formed into a single-sided air inlet structure; and the fan blade is configured to guide air from the air inlet on a single side to the at least one first air outlet for blowing out.

Compared with the prior art, the neck fan provided by the present disclosure has the advantages that the at least one air inlet is provided in one of the first side and the second side, and the other side has no air inlet, thus forming a single-sided air inlet structure and supplying air from a single side. During use of the neck fan, the hairs can be placed on the side of each housing provided with no air inlet, to avoid the hairs from being entangled into the air inlet, which also reduces the possibility that dust and impurities enter the product, avoids a product failure, and improves the reliability of the product. In addition, when the fan blade groups with the first centrifugal vane wheels and the second centrifugal vane wheels both use the design in which the air inlet is provided in one side, the adverse effect caused by low air intake efficiency of single-sided air supplying can be reduced, and the air intake volume and the air intake efficiency of the neck fan are improved. Thus, the blowing force and the air discharging volume are ensured; the air discharging effect is ensured; and the cooling effect is enhanced.

In addition, in some embodiments, the first enclosure wall and the second enclosure wall are respectively mounted and wound at the peripheries of the circuit board and the battery, which can ensure that rainwater, sweat, or the like can be isolated outside the circuit board and the battery after entering the accommodating cavities from a gap such as the air inlet or the air outlet, thus avoiding the water from wetting the battery and the circuit board. This achieves a waterproof effect, reduces product failure, and ensures the safety and service life of the product.

BRIEF DESCRIPTION OF THE DRAWINGS

In order to explain the technical solutions of the embodiments of the present invention more clearly, the following will briefly introduce the accompanying drawings used in the embodiments. Apparently, the drawings in the following description are only some embodiments of the present invention. Those of ordinary skill in the art can obtain other drawings based on these drawings without creative work.

The present invention is further described below in detail in combination with the accompanying drawings and embodiments.

DETAILED DESCRIPTION OF THE EMBODIMENTS

Figure 1:
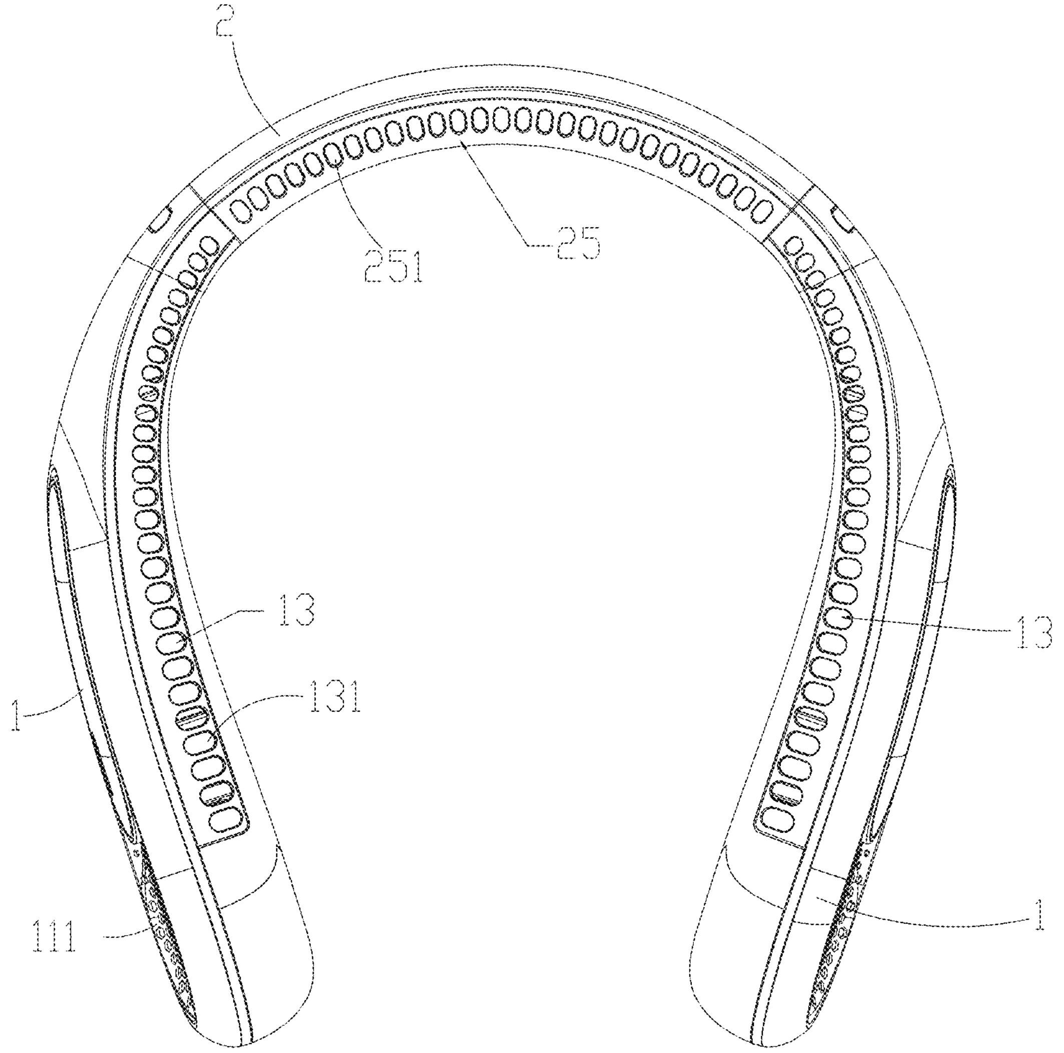
FIG. 1 is a three-dimensional diagram of a neck fan according to an embodiment of the present disclosure.
Figure 2:
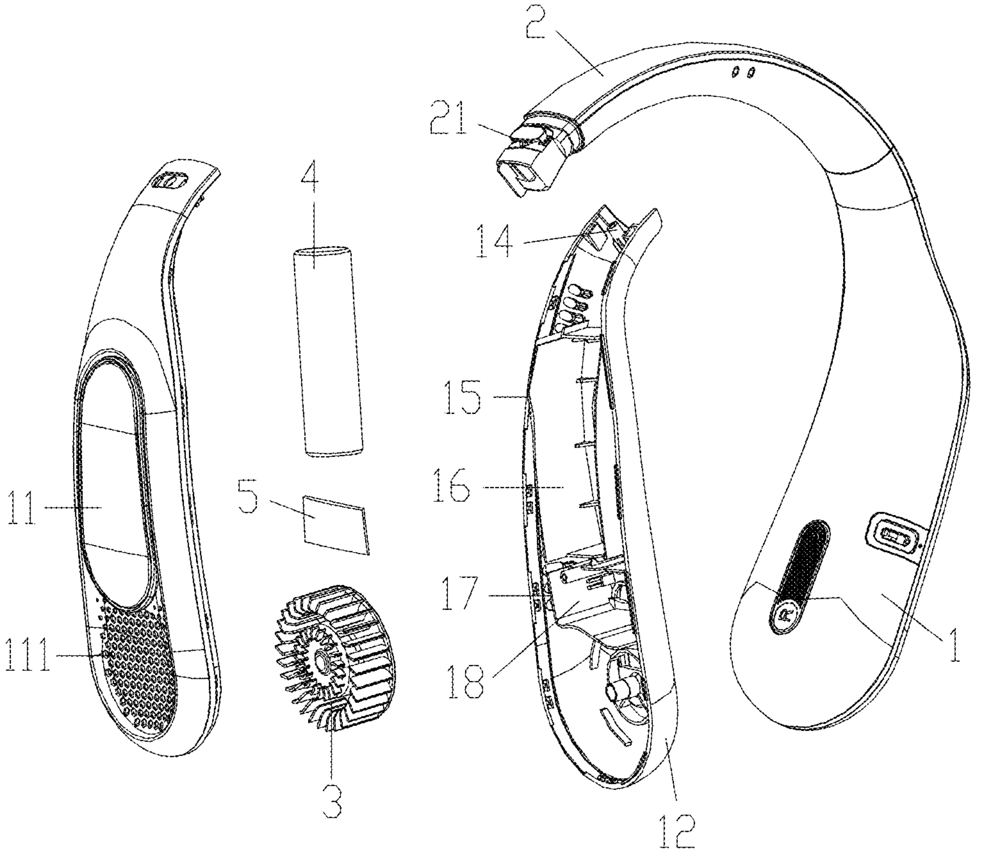
FIG. 2 is a partially exploded view of a neck fan according to an embodiment of the present disclosure.

The technical solutions in the embodiments of the present invention will be clearly and completely described below in conjunction with the accompanying drawings in the embodiments of the present invention. Apparently, the described embodiments are only a part of the embodiments of the present invention, rather than all the embodiments. Based on the embodiments in the present invention, all other embodiments obtained by those ordinarily skilled in the art without doing creative work shall fall within the protection scope of the present invention.

Referring to FIG. 1 to FIG. 10, an embodiment of the present disclosure provides a neck fan 100.

The neck fan 100 includes a neck fan main body 10, a circuit board 5, and a battery 4 electrically connected to the circuit board 5. A first enclosure wall 17 that is enclosed to form a first mounting cavity 18 and a second enclosure wall 15 that is enclosed to form a second mounting cavity 16 are provided in the neck fan main body 10. The circuit board 5 is mounted in the first mounting cavity 18, and the battery 4 is mounted in the second mounting cavity 16.

In the present disclosure, the circuit board 5 is mounted through the first enclosure wall 17, and the battery 4 is mounted through the second enclosure wall 15. In raining days, when rainwater falls from an air inlet 111 or a first air outlet 13, the rainwater can be effectively isolated by the first enclosure wall 17 and the second enclosure wall 15, thus preventing the rainwater from wetting the battery 4 and the circuit board 5, playing a waterproof role, and solving the problem of the existing neck fan that the circuit board 5 and the battery 4 easily gets wet if the rainwater or sweat falls into the neck fan from the first air outlet 13.

In an embodiment, the first enclosure wall 17 is provided with a first wiring slot 171 on a side wall opposite to the second enclosure wall 15, and the first wiring slot 171 is communicated to the first mounting cavity 18. The second enclosure wall 15 is provided with a second wiring slot 155 at a position corresponding to the first wiring slot 171, and the second wiring slot 155 is communicated to the second mounting cavity 16. Through the first wiring slot 171 and the second wiring slot 155, it is convenient to route a first wire 176 electrically connected to the circuit board 5 and the battery 4.

In an embodiment, fan blade groups 3 electrically connected to the circuit board 5 are arranged at two ends inside the neck fan main body 10. The circuit board 5 is located between the fan blade groups 3 and the battery 4. Honeycomb-shaped air inlets 111 are provided in positions, corresponding to the fan blade groups 3, on an outer side wall of the neck fan 100. A first air outlet 13 communicated to the inside is provided in an inner side of the neck fan main body 10, and the first wiring slot 171 is located on one side away from the first air outlet 13. Specifically, a region of the air inlets 111 is the same as that of the fan blade groups 3, which effectively enhances the air supplying effect.

In an embodiment, each fan blade group 3 includes a motor 35, a first centrifugal vane wheel 32 connected to the motor 35, and a second centrifugal vane wheel 31 arranged on an outer side of the first centrifugal vane wheel 32. The first centrifugal vane wheel 32 is connected to the second centrifugal vane wheel 31. By configuring the first centrifugal vane wheel 32 and the second centrifugal vane wheel 31, the blowing force of the neck fan 100 of the present disclosure can be increased, and the cooling effect can be enhanced.

In an embodiment, each fan blade group 3 further includes a boss 34 and an annular base plate 33 arranged on an outer side of the boss 34. The second centrifugal vane wheel 31 is arranged on the annular base plate 33. The first centrifugal vane wheel 32 is arranged on the boss 34. The motor 35 is at least partially arranged inside the boss 34, and a rotating shaft of the motor is connected to the boss 34 to integrate the first centrifugal vane wheel 32 with the second centrifugal vane wheel 31, so that the first centrifugal vane wheel 32 and the second centrifugal vane wheel 31 can be simultaneously driven to rotate when the motor 35 is driven.

In an embodiment, the first air outlet 13 is a plurality of through holes. The plurality of through holes are arranged in a length direction of the neck fan 100, which can effectively increase air discharging directions and enhance the cooling effect when the neck fan is worn at the neck. An air guide plate 19 is arranged inside the neck fan main body 10. The air guide plate 19 includes: a first separation section for separating the circuit board 5 from each fan blade group 3, a second separation section 192 connected to the first separation section 193 and arranged along a length of the first air outlet 13, and an air guide portion 191 connected to one end of the second separation section 192 away from the first separation section 193 and extending to the first air outlet 13. An air flow generated by the fan blade group 3 can be effectively discharged from the first air outlet 13 under the action of the air guide plate 19, thereby enhancing the cooling effect.

In an embodiment, the first enclosure wall 17 includes a first enclosure plate 173, a second enclosure plate 175, and a third enclosure plate 172 which are connected in sequence. The first enclosure plate 173 and the second enclosure plate 175 are spaced apart, and one end of the first enclosure plate 173 and one end of the second enclosure plate 175 are connected to an inner side wall of the neck fan main body 10. The first mounting cavity 18 is formed by enclosing the first enclosure wall 17 and the inner side wall of the neck fan main body 10. The second enclosure wall 15 includes a fourth enclosure plate 154, a fifth enclosure plate 152, a sixth enclosure plate 151, and a seventh enclosure plate 153 which are connected in sequence. The fourth enclosure plate 154 and the sixth enclosure plate 151 are spaced apart, and one end of the fourth enclosure plate 154 and one end of the sixth enclosure plate 151 are connected to the inner side wall of the neck fan main body 10. The first wiring slot 171 is located on the third enclosure plate 172, and the second wiring slot 155 is located on the fourth enclosure plate 154. The first separation section 193 is the first enclosure 173, and the second separation section 192 is composed of the second enclosure 175 and the fifth enclosure 152, to effectively reduce structures during the formation of the air guide plate 19. The first wiring slot 171 and the second wiring slot 155 are arranged in sequence in an extension direction of a blowing housing 1.

In the above embodiments, for the compactness of the structure of the present disclosure, the neck fan main body 10 includes a neck support 2 and blowing housings 1 arranged at two ends of the neck support 2. The first enclosure wall 17, the second enclosure wall 15, the fan blade group 3, the air inlet 111, and the first air outlet 13 are all located inside each blowing housing 1.

It can be understood that each blowing housing 1, and the fan blade groups 3, the first enclosure wall 17, the second enclosure wall 15, the battery 4, the circuit board 5, and other elements which are located in the blowing housing 1 can constitute a blowing main body 1*c*. Therefore, the neck fan main body 10 can specifically include two blowing main bodies 1*c* and a neck support 2 connected between the two blowing main bodies 1*c*. The neck support 2 is configured to be in contact with the neck of a user to hang the neck fan main body 10 around the neck of the user, and the two blowing main bodies 1*c* are respectively configured to be arranged on two sides of the neck of the user to blow air towards the user. In some change implementations, the neck support may be omitted, so that the two blowing main bodies 1*c* are directly connected.

Each blowing housing 1 includes a first housing 11 and a second housing 12 connected to the first housing 11. A first partition plate 113 and a second partition plate 112 protrude out of and are formed on an inner side wall of the first housing 11, and a third partition and a fourth partition 156 protrude out of and are formed on an inner side wall of the second housing 12. The first partition plate 113 and the third partition plate resist against to form the first enclosure wall 17, and the second partition plate 112 and the fourth partition plate 156 resist against to form the second enclosure wall 15, to effectively play a waterproof role. In this embodiment, the third partition plate is integrated with the third enclosure plate 172.

In an embodiment, a plug-in column 14 protrudes out of and is formed on the inner side wall of the second housing 12, and a plug-in hole 21 is provided in the neck support 2. The plug-in column 14 is inserted into the plug-in hole 21 when the first housing 11 is connected to the second housing 12. By the cooperation between the plug-in column 14 and the plug-in hole 21, the neck support 2 can be connected.

Figure 7:
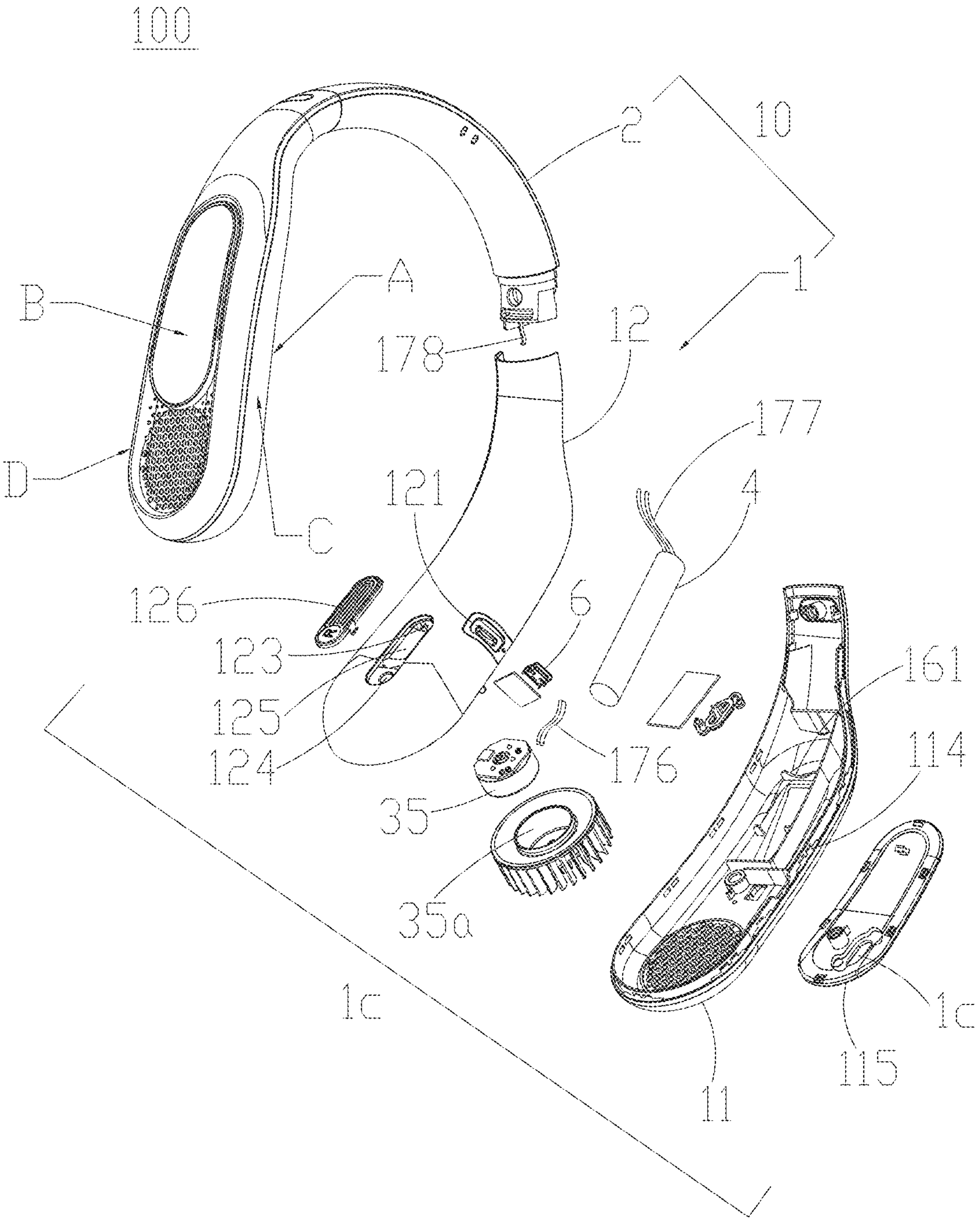
FIG. 7 is a partially exploded view of a neck fan according to an embodiment of the present disclosure, viewed in another angle.
Figure 8:
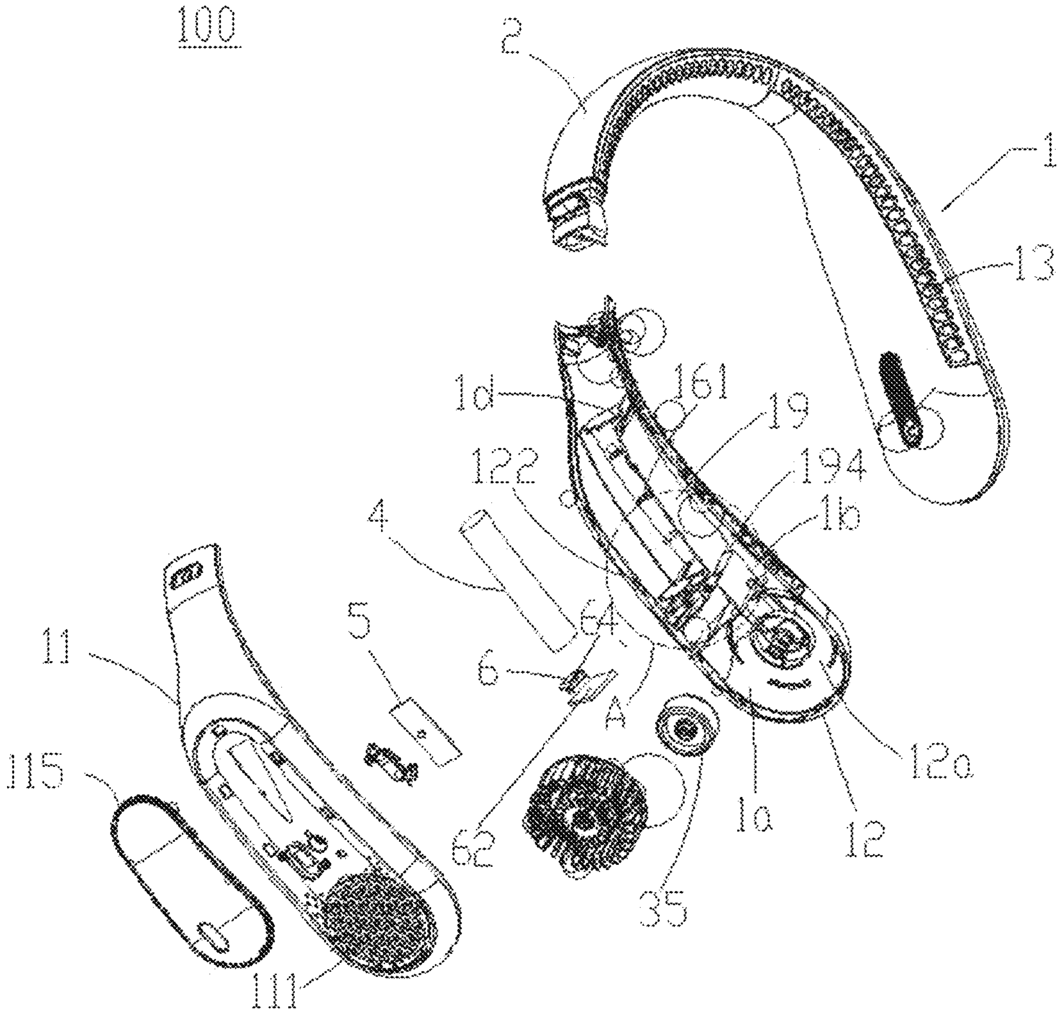
FIG. 8 is a partially exploded view of a neck fan according to an embodiment of the present disclosure, viewed in still another angle.
Figure 9:
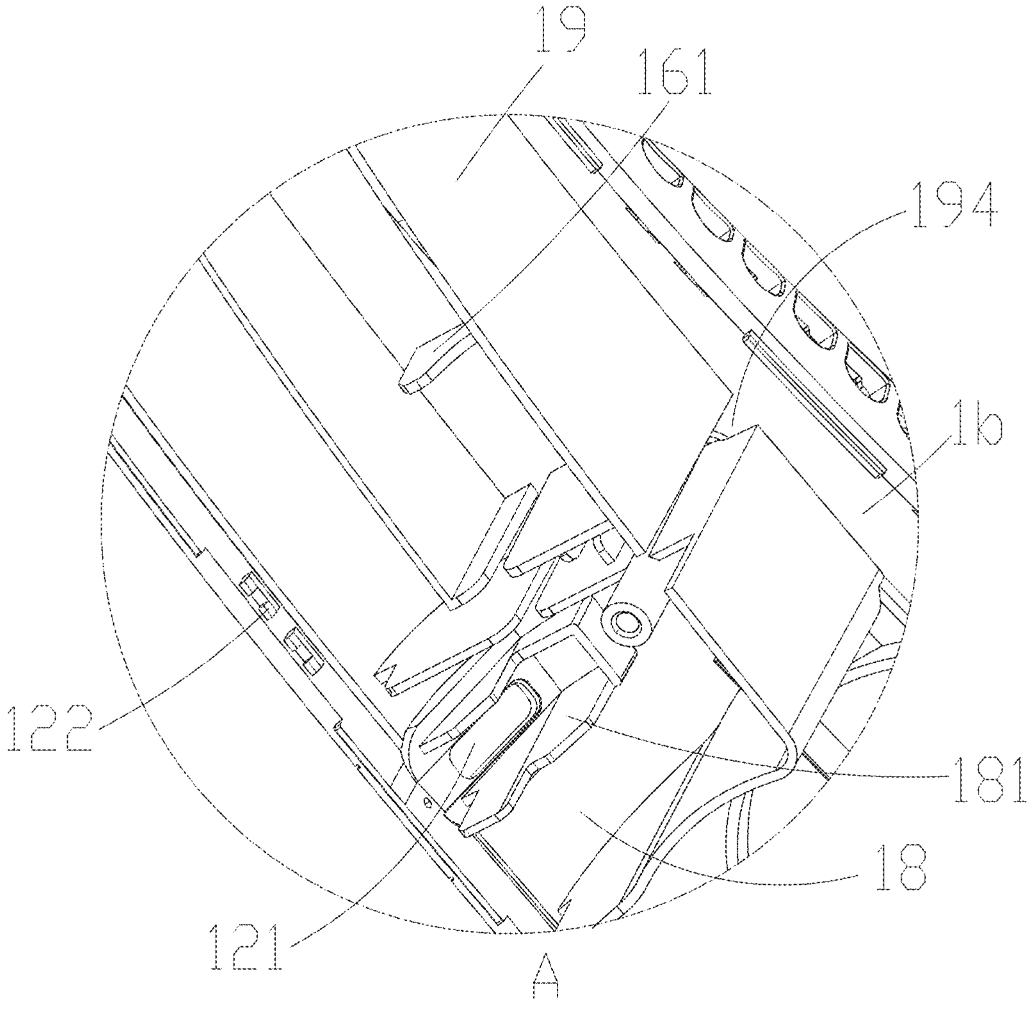
FIG. 9 is an enlarged view of part A in FIG. 8.

Referring to FIG. 7, FIG. 8, and FIG. 9, the first housing 11 and the second housing 12 are respectively provided with a first buckle 114 and a second buckle 122. The first buckle 114 and the second buckle 122 are buckled with each other to connect the first housing 11 with the second housing 12. A plurality of first buckles 114 and a plurality of second buckles 122 are provided and are arranged in a one-to-one correspondence manner. In this embodiment, the first buckles 114 are clamping slots or clamping holes provided in the first housing 11, and the second buckles 122 are clamping blocks arranged on the second housing 12. When the first buckles 114 are buckled with the second buckles 122, the clamping blocks are clamped into the clamping slots or clamping holes. In other embodiments, the first buckles 114 may be clamping slots or clamping holes provided in the second housing, and the second buckles 122 may be clamping blocks arranged on the first housing. Alternatively, both the first buckles 114 and the second buckles 122 are hooks or other structures that can achieve interlocking.

Specifically, the first housing 11 and the second housing 12 are connected to form an accommodating cavity 1*a*, and the first mounting cavity 18, the second mounting cavity 16, and a first air duct 1*b* are all located inside the accommodating cavity 1*a*. The battery 4, the circuit board 5, and the fan blade group 3 are all arranged in the accommodating cavity 1*a*. To ensure the waterproof effect, the first enclosure wall 17 and the second enclosure wall 15 both resist against inner walls of the first housing 11 and the second housing 12, thereby preventing rainwater and the like from entering the first mounting cavity 18 and the second mounting cavity 16. The first enclosure wall 17 is arranged on at least three sides of the circuit board 5. The second enclosure wall 15 is wound around at least three sides of the battery 4. Two end portions of the air guide plate 19 respectively resist against the inner walls of the first housing 11 and the second housing 12, thereby enclosing the first housing 11 and the second housing 12 to form the first air duct 1*b*. This can reduce the loss of the air flow generated by the fan blade group 3, so that the air flow flows out of the first air outlet 13 after passing through the first air duct 1*b*, which enhances the air discharging effect. A decorative sheet 115 is further arranged on one side of the first housing 11 away from the second housing 12, making the appearance of the product neater and more beautiful.

The neck fan 100 provided in this embodiment is configured be worn around the neck of the user.

Referring to FIG. 7 and FIG. 8, the neck fan main body 10 is of a U-shaped structure. In this way, the neck fan 100 can be worn around the neck of the user, facilitating use. Each blowing housing 1 includes a first side A, a second side B opposite to the first side A, a third side C adjacent to the first side A and the second side B, and a fourth side D adjacent to the third side C.

For ease of understanding and description, the first side A is an inner side for approaching the neck of the user, and the second side B is an outer side arranged in a back-to-back manner with the inner side; at least one air inlet 111 is provided in the second side B; the fourth side D is a bottom side for being in contact with a shoulder of a human body; and the third side C is a top side corresponding to the head of the human body. Specifically, the first housing 11 is located on the second side B of the blowing housing 1, and the second housing 12 is located on the first side A of the blowing housing 1.

In this embodiment, the air inlet 111 is provided in the first housing 11, that is, the air inlet 111 is located on the second side B of the blowing housing 1. When the user wears the neck fan 100 around the neck, the air inlet 111 is located on one side (i.e., the outer side) of the neck fan 100 farther away from the user. This design can not only avoid the hairs from entering the air inlet 111, but also improve the air intake volume and the air intake efficiency, and can avoid air interference caused by the opposite arrangement of the air inlets on two sides when the air inlets are provided in the inner side. Since no air inlet is provided in the second side B of the blowing housing 1, namely, since no air inlet is provided in the second housing 12, the blowing housing 1 forms a single-sided air inlet structure. The air inlet 111 corresponds to the first centrifugal vane wheel 32 and the second centrifugal vane wheel 31, so that the first centrifugal vane wheel 32 and the second centrifugal vane wheel 31 guide air from the air inlet 111 on the single side to the first air outlet 13 for blowing out. This can reduce the adverse effect caused by low air intake efficiency of single-sided air supplying, improve the air intake volume and air intake efficiency of the neck fan, and ensure the blowing force and the air discharging volume, thereby ensuring the air discharging effect and enhancing the cooling effect.

The first air outlet 13 is provided in the second housing 12. Specifically, the first air outlet 13 is provided in the fourth side D of the blowing housing 1. The first air outlet 13 includes a plurality of first air outlet holes 131. The plurality of first air outlet holes 131 are arranged in sequence in the extension direction of the second housing 12. In addition, in this embodiment, a second air outlet 25 is provided in the neck support 2. The second air outlet 25 includes a plurality of second air outlet holes 251 arranged in the extension direction of the neck support 2.

Specifically, the accommodating cavity **1*a* has a mounting portion 12*a* for mounting the fan blade group 3. The neck fan main body 10 further has a first wiring hole 123, a second wiring hole 124, and a third wiring slot 125. The first wiring hole 123 is communicated to the first mounting cavity 18. The second wiring hole 124 corresponds to and is communicated to the mounting portion 12*a*. The third wiring slot 125 is arranged on one side of the neck fan main body 10 away from the accommodating cavity 1*a* and is communicated between the first wiring hole 123 and the second wiring hole 124. The third wiring slot 125 is configured to accommodate a second wire 177 electrically connected between the fan blade group 3 and the circuit board 5**.

The third wiring slot 125 is provided in the first side A and back onto the air inlet 111. The neck fan 100 further includes a decorative cover 126. The decorative cover 126 is mounted corresponding to the third wiring slot 125 and is connected to the blowing housing 1, so that a surface of the first side A of the blowing housing 1 is smoothly connected to an outer surface of the decorative cover 126 after mounting. Specifically, the decorative cover 126 is further provided with a wearing identification (e.g. R and L), where R represents the right side and L represents the left side. For convenience of manufacturing, the wearing identification can be integrally formed with the decorative cover 126, but not limited to the above, and a wearing identification like a sticker can be used too.

The decorative cover 126 is in buckled connection with the blowing housing 1. The decorative cover 126 includes a plurality of hooks. The blowing housing 1 includes a plurality of bayonets. The hooks are clamped to the bayonets. The plurality of bayonets are respectively adjacent and communicated to the first wiring hole 123 and the second wiring hole 124.

In this embodiment, the fan blade group 3 is arranged corresponding to the air inlet 111, so that external air is directly driven by the fan blade group 3 after passing through the air inlet 111, which shortens an air flowing path. Then, the fan blade group 3 pushes the air to generate an air flow, and the air flow flows out through the first air outlet 13, thereby cooling the user. The air inlet 111 is of a single hole structure. A plurality of air inlets 111 are arranged in a honeycomb. In other embodiments, the plurality of air inlets 111 may be arranged in another array. The arrangement of the plurality of air inlets 111 can ensure the air intake volume and reduce the probability of hairs or dust impurities entering the neck fan 100, thereby reducing the failure rate of the product and prolonging the service life of the product.

Figure 3:
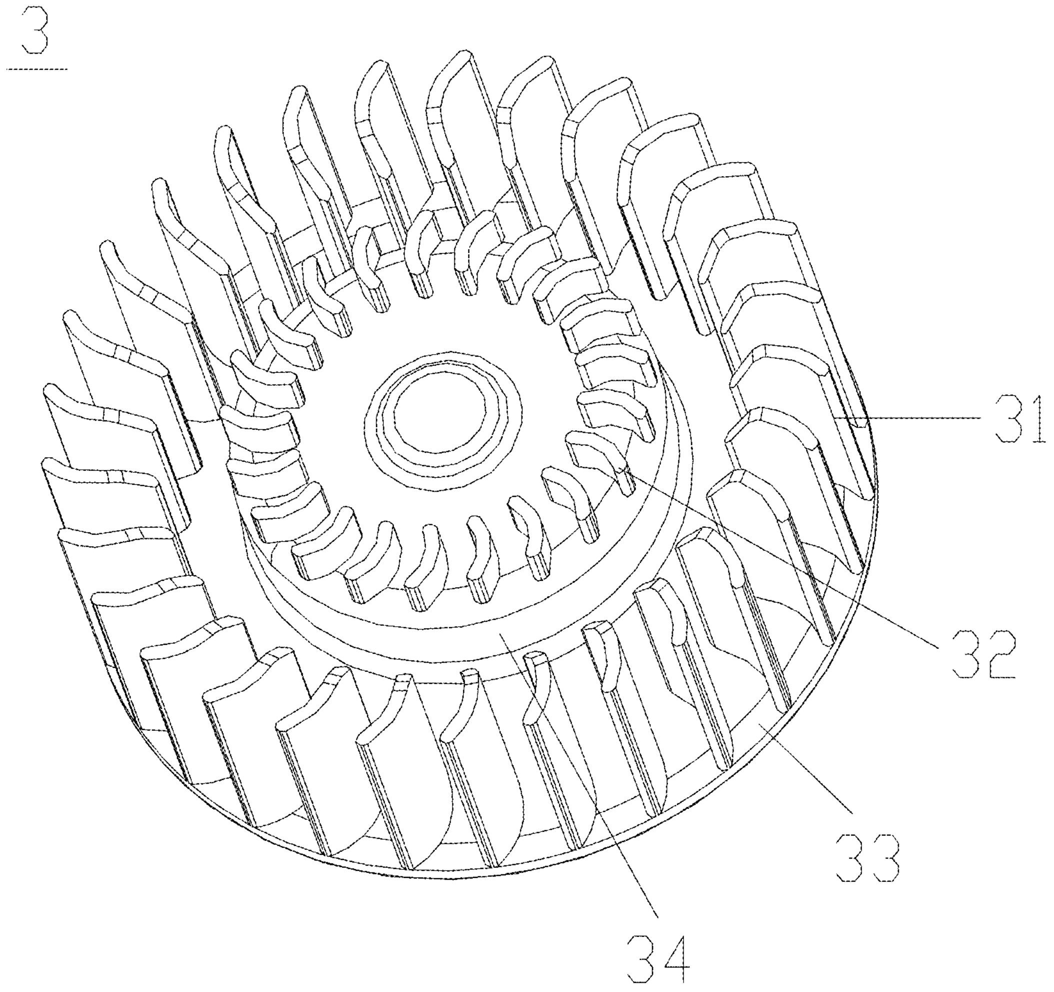
FIG. 3 is a partially structural diagram of a fan blade group of a neck fan according to an embodiment of the present disclosure.
Figure 4:
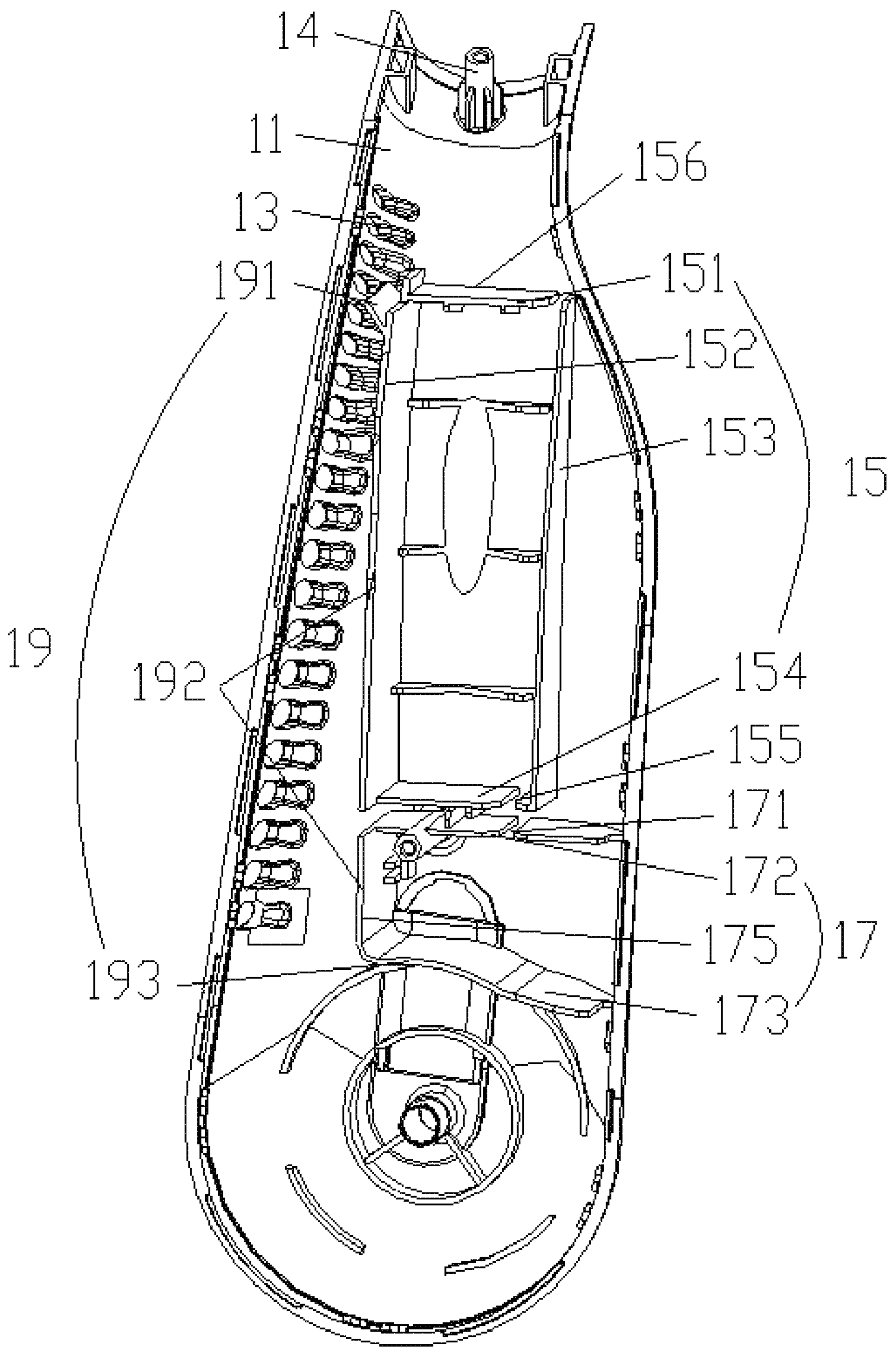
FIG. 4 is a structural diagram of a second housing of a neck fan according to an embodiment of the present disclosure.
Figure 5:
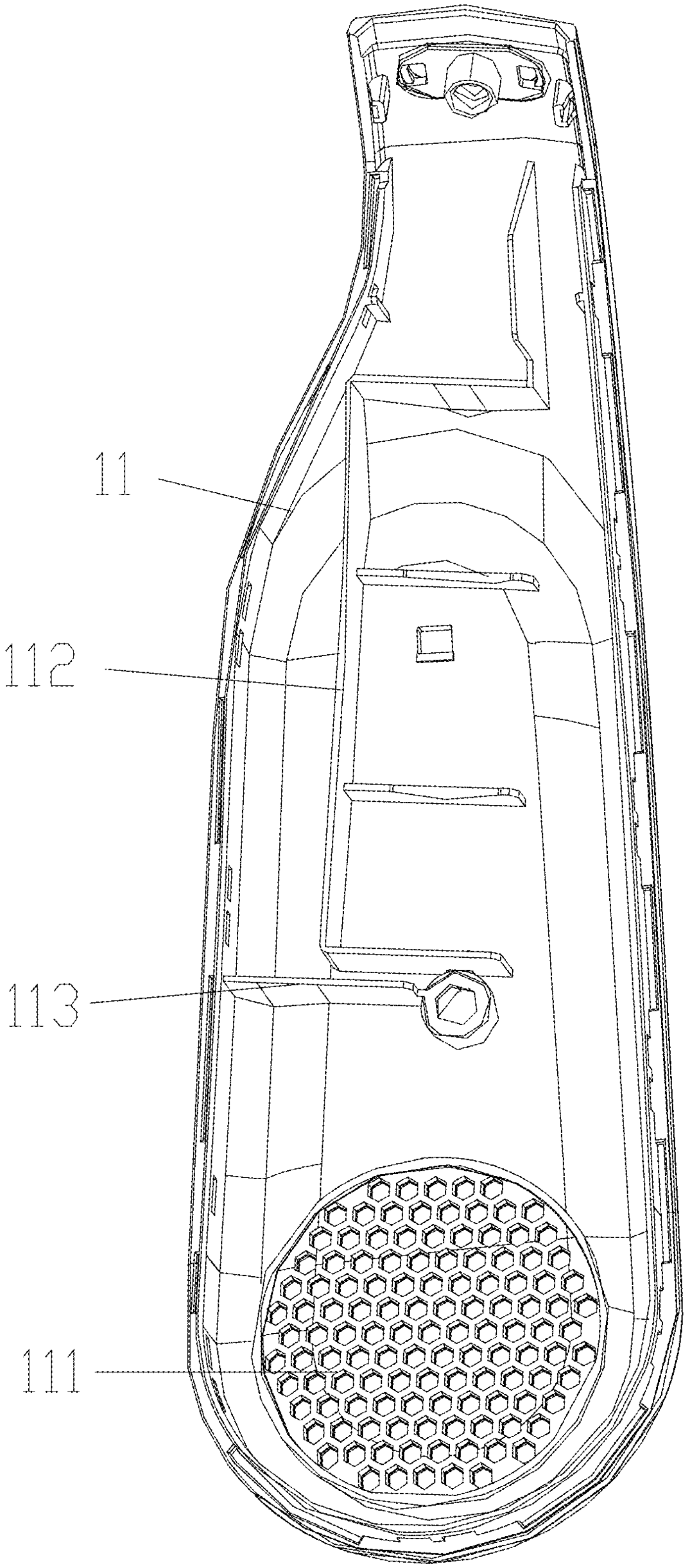
FIG. 5 is a structural diagram of a first housing of a neck fan according to an embodiment of the present disclosure.
Figure 6:
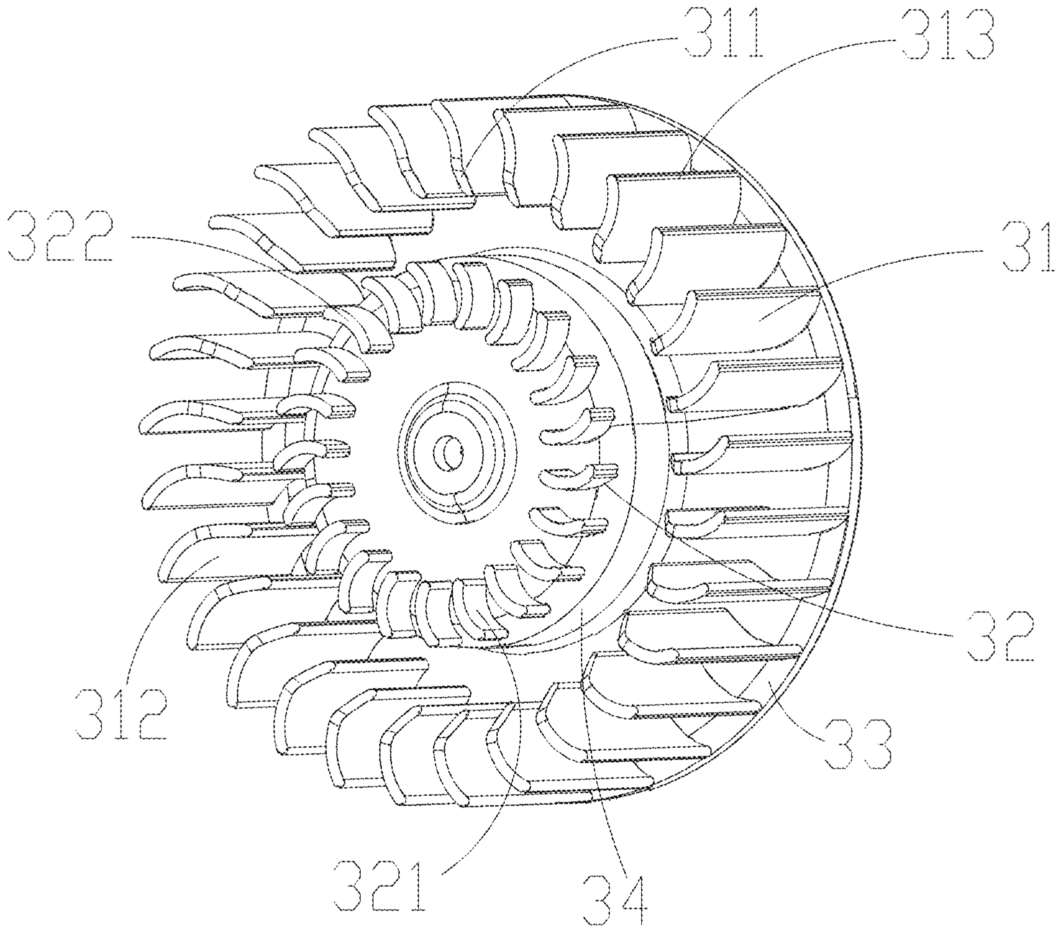
FIG. 6 is a partially structural diagram of a fan blade group of a neck fan according to an embodiment of the present disclosure, viewed in another angle.

Referring to FIG. 3 and FIG. 6, in this embodiment, a cross section of the boss 34 and a cross section of the annular base plate 33 in a direction perpendicular to an axis are circular. A central axis of the boss 34 overlaps a central axis of the annular base plate 33, and an axial direction of a rotating shaft of the motor 35 overlaps the central axis. The first centrifugal vane wheel 32 includes a plurality of first blades 322 arranged around a preset axial direction, and the second centrifugal vane wheel 31 includes a plurality of second blades 313 arranged around the preset axial direction. The first blades 322 and the second blades 313 are both arc-shaped blades. A length of each first blade 322 is less than a length of the second blade 313. A bending direction of the first blade 322 and a bending direction of the second blade 313 are the same. A curvature of the first blade 322 is greater than a curvature of the second blade 313. A height of the first blade 322 in the preset axial direction is less than a height of the second blade 313 in the preset axial direction.

Specifically, each second blade 313 of the second centrifugal vane wheel 31 has an air outlet surface 312, and the air outlet surfaces 312 of the plurality of second blades 313 are arranged in a first direction. A plurality of first blades 322 are uniformly arranged on inner sides of a plurality of second blades 313 around the central axis. The first centrifugal vane wheel 32 has an air guide surface 321. The air guide surfaces 321 of the plurality of first blades 322 are arranged in the first direction, that is, an arrangement direction of the plurality of first blades 322 is the same as an arrangement direction of the plurality of second blades 313, to reduce the possibility of turbulence generated on the inner sides of the plurality of second blades 313 through the plurality of first blades 322.

It should be noted that the first direction can be clockwise or counterclockwise. The air outlet surfaces 312 of the plurality of second centrifugal vane wheels 31 are arranged in the first direction, and the air guide surfaces 321 of the plurality of first centrifugal vane wheels 32 are arranged in the first direction.

To enhance the air outlet effect, the air outlet surfaces 312 of the second centrifugal vane wheels 31 are arc-shaped. That is, each second centrifugal vane wheel 31 protrudes to one side and bends to form a curvature. The air guide surfaces 321 of the first centrifugal vane wheels 32 are arc-shaped. That is, each first centrifugal vane wheel 32 protrudes to one side and bends to form a curvature. In this embodiment, the first centrifugal vane wheel 32 and the second centrifugal vane wheel 31 protrude in the same direction, i.e., bend in the same direction, so that air entering the fan blade group 3 through the air inlet 111 is further pushed by the first centrifugal vane wheel 32 after entering the second centrifugal vane wheel 31, so that an initial wind speed of the air flow generated by the fan blade group 3 is increased, and the blowing force is increased. Meanwhile, the two groups of centrifugal vane wheels also ensure an increase in the air discharging volume, thereby ensuring the air outlet effect and enhancing the cooling effect.

To ensure that the air flow generated by the first centrifugal vane wheel 32 smoothly enters the second centrifugal vane wheel 31 and is further pushed, a height of the boss 34 in an axial direction of the annular base plate 33, namely, in a thickness direction of the annular base plate 33, is less than a height of the second centrifugal vane wheel 31. In this embodiment, a sum of the height of the first centrifugal vane wheel 32 and the height of the boss 34 is roughly equivalent to the height of the second centrifugal vane wheel 31, that is, one end of the first centrifugal vane wheel 32 away from the boss 34 is roughly flush with one end of the second centrifugal vane wheel 31 away from the annular base plate 33. The boss 34 is integrally formed with the annular base plate 33.

In this embodiment, a flow guide portion 311 is arranged at one end of the second centrifugal vane wheel 31 away from the annular base plate 33, and a height of one side of the flow guide portion 311 close to the boss 34 is less than a height of one side of the flow guide portion 311 away from the boss 34. Tilting a top end of one side, close to the boss 34, of the second centrifugal vane wheel 31 can allow a portion of the air flow from the first centrifugal vane wheel 32 to flow along an inclined surface of the flow guide portion 311 under the action of the flow guide portion 311, and the remaining air flow enters the second centrifugal vane wheel 31, thereby reducing the noise of the fan blade group 3 and increasing the air discharging volume. Meanwhile, the impact of the second centrifugal vane wheel 31 on an air flow velocity can be reduced, thereby ensuring the air discharging effect.

To facilitate the mounting of the motor 35 and reduce the volume of the product, the boss 34 is further formed with a motor accommodating slot 35*a* on one side away from the first centrifugal vane wheel 32, and the motor 35 is arranged in the motor accommodating slot 35*a*.

Referring to FIG. 7 and FIG. 8, the air guide plate 19 and the neck fan main body 10 are enclosed to form the first air duct 1*b*. The first air duct 1*b* is communicated to the first air outlet 13. The fan blade group 3 discharges the generated air flow through the first air duct 1*b* from the first air outlet 13, thereby blowing air to achieve cooling.

To take away heat generated by both the battery 4 and the circuit board 5, in this embodiment, an opening 194 is provided in the second separation section 192, which can allow a portion of the air flow in the first air duct 1*b* to flow through the first mounting cavity 18 and the second mounting cavity 16 when passing through the opening 194, to take away the heat generated by both the battery 4 and the circuit board 5 and play a cooling role. Specifically, to make the cooling effect better, the opening 194 is communicated to the first wiring slot 171 and the second wiring slot 155, which allows the air flow to enter the first mounting cavity 18 and the second mounting cavity 16 deeply to directly take away the heat. Meanwhile, if there are water stains inside, the air flow can quickly dry the water stains, to ensure that environments inside the first mounting cavity 18 and the second mounting cavity 16 are dry.

For ease of charging, the neck fan main body 10 is provided with a charging port component 6. The charging port component 6 is electrically connected to the circuit board 5 for connecting an external power supply to charge the battery 4, so that the neck fan 100 can be carried and used. Specifically, the neck fan main body 10 is provided with a mounting hole 121 for exposing the charging port component 6. The charging port component 6 is arranged in the mounting hole 121 in a penetrating manner and is electrically connected to the circuit board 5, and the charging port component 6 comprises a main circuit board 62 and a charging port 64, the main circuit board 62 is penetrated in the mounting hole 121 in a direction substantially perpendicular to a surface of the one of the blowing main bodies 1*c*, and the charging port 64 is exposed at the surface of the one of the blowing main bodies 1*c*. The mounting hole 121 is communicated to the first mounting cavity 18, and the mounting hole 121 does not overlapped with the first air duct 1*b* along the lengthwise direction of the one of the blowing main bodies 1*c*. To fix the charging port component 6 and prevent the charging port component 6 from moving or shaking, a first limiting member 181 is arranged in the first mounting cavity 18. The first limiting member 181 is adjacent to the mounting hole 121 and surrounds a periphery of the charging port component 6. The first limiting member 181 is connected to an inner wall of the neck fan main body 10 and resists against the charging port component 6, thus ensuring that the charging port component 6 is restrained in the mounting hole 121 and avoiding movement or shaking of the charging port component 6 during use. This prolongs the service life of the product.

In this embodiment, the charging port component 6 is arranged on one of the blowing housings 1, specifically on one of the second housings 12. The batteries 4 at the two ends are electrically connected using a third wire 178. In other embodiments, charging port components 6 may be arranged on the two blowing housings 1.

In this embodiment, each battery 4 uses a cylindrical structure, which has a battery top side and a battery bottom side. The battery top side and the battery bottom side are opposite to each other and adjacent to a periphery of the battery 4. To mount battery 4 more stably, a second limiting member 161 is arranged in the second mounting cavity 16. The second limiting member 161 resists against the battery 4 and cooperates with the second enclosure wall 15 to limit the battery 4 in the second mounting cavity 16, to avoid the battery 4 from shaking or moving, thereby reducing wear and noise. In this embodiment, the second enclosure wall 15 is wound around the periphery of the battery 4. A plurality of second limiting members 161 are provided, which respectively resist against the periphery, the battery top side, and the battery bottom side of the battery 4. In other embodiments, the battery 4 may be of a structure in another shape, such as a cuboid structure, and the second limiting member 161 may be designed according to the shape and structure of the battery 4, to stably fix the battery 4.

Figure 10:
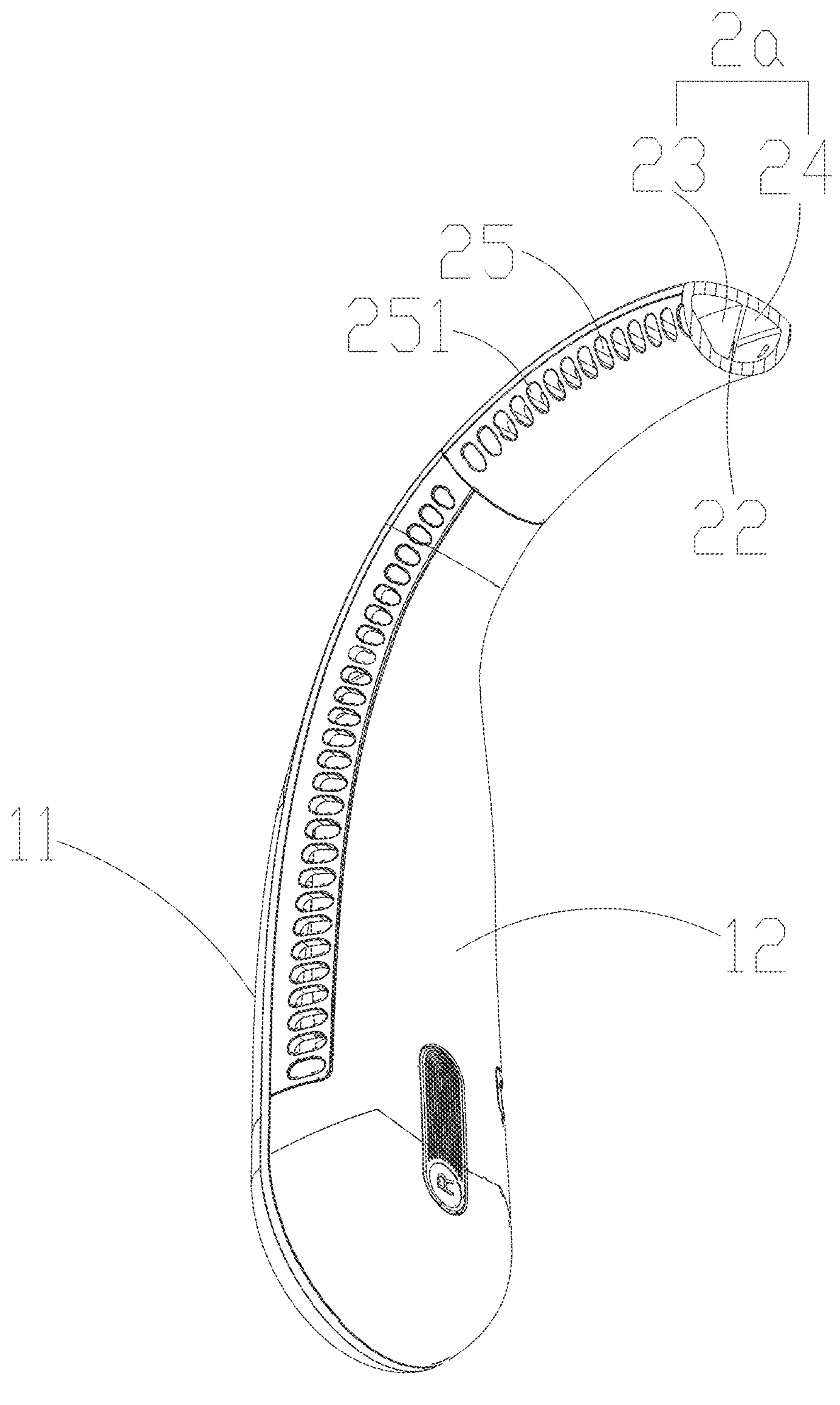
FIG. 10 is a sectional view of a neck support of a neck fan according to an embodiment of the present disclosure.

Referring to FIG. 10, to convey the air flow to the second air outlet 25 on the neck support 2, a cavity 2*a* which penetrates through the neck support 2 in a length direction of the neck support is provided in the neck support 2. The cavity 2*a* is communicated to the accommodating cavities 1*a* inside the blowing housings 1 at the two ends. The second air outlet 25 on the neck support 2 is communicated to the cavity 2*a*.

Specifically, a separation plate 22 is arranged inside the neck support 2. The separation plate 22 extends in a length direction of the neck support 2 to divide the cavity 2*a* into a second air duct 23 and a threading cavity 24. The second air duct 23 is communicated to the second air outlet 25 on the neck support 2, and the second air duct 23 is further communicated to the first air duct 1*b*, so that the air flow generated by the fan blade group 3 can be conveyed through the first air duct 1*b* to the second air duct 23, and then flow out through the second air outlet 25 on the neck support 2. Specifically, each blowing housing 1 is further provided with the air guide portion 191, which guides the air flow in the first air duct 1*b* to the second air duct 23. The air guide portion 191 is connected to one end of the second enclosure wall 15 away from the first enclosure wall 17, and the air guide portion 191 gradually approaches the first air outlet holes 131 away from the fan blade group 3. The threading cavity 24 is configured to thread the third wire 178 electrically connected to electronic devices inside the blowing housings 1 located at the two ends of the neck support 2. Thus, separation of the wire from the air flow is achieved, which avoids mutual impact and ensures the safety of electricity use.

As described above, one or more embodiments are provided in conjunction with the detailed description, The specific implementation of the present invention is not confirmed to be limited to that the description is similar to or similar to the method, the structure and the like of the present invention, or a plurality of technical deductions or substitutions are made on the premise of the conception of the present invention to be regarded as the protection of the present invention.

What is claimed is:

1. A neck fan, configured to be worn around the neck of a user, and comprising:

a neck fan main body, comprising two blowing main bodies respectively configured to be arranged on two sides of the neck of the user, wherein each blowing main body comprises a blowing housing; the blowing housing forms an accommodating cavity and is provided with at least one air inlet communicated to the accommodating cavity and at least one first air outlet communicated to the accommodating cavity;

fan blade groups, arranged in the accommodating cavities, wherein each fan blade group comprises a boss, an annular base plate arranged on an outer side of the boss, a first centrifugal vane wheel arranged on the boss and comprising a plurality of first blades, and a second centrifugal vane wheel arranged on the base plate and comprising a plurality of second blades; the first centrifugal vane wheel and the second centrifugal vane wheel are arranged on a same side relative to the base plate, and the second centrifugal vane wheel is arranged around a periphery of the first centrifugal vane wheel, the first blades are arranged on a top surface of the boss away from the base plate, a sum of a height of the first centrifugal vane wheel and a height of the boss is substantially equivalent to a height of the second centrifugal vane wheel, and a bending direction of each of the first blades and a bending direction of each of the second blades are the same;

each blowing housing comprises a first side, a second side opposite to the first side, a third side adjacent to the first side and the second side, and a fourth side adjacent to the third side, the first side is an inner side for approaching the neck of a user, and the second side is an outer side arranged in a back-to-back manner with the inner side;

the at least one air inlet is provided in the second side, and corresponds to the first centrifugal vane wheel and the second centrifugal vane wheel; the first side has no air inlet, so that the blowing housing is formed into a single-sided air inlet structure, thereby when the first side approaches the neck of the user, hairs of the user can be avoided from being entangled into the air inlet on the second side; and the first centrifugal vane wheel and the second centrifugal vane wheel are configured to guide air from the air inlet on a single side to the at least one first air outlet for blowing out.

2. The neck fan according to claim 1, wherein the fourth side is a bottom side for being in contact with a shoulder of a human body; and the third side is a top side corresponding to the head of the human body.

3. The neck fan according to claim 2, further comprising a circuit board, wherein the circuit board is electrically connected to the fan blade groups; a first enclosure wall that is enclosed to form a first mounting cavity is arranged inside the accommodating cavity; the first enclosure wall is connected to the blowing housings; the circuit board is arranged in the first mounting cavity; and the first enclosure wall is arranged on at least three sides of the circuit board.

4. The neck fan according to claim 3, wherein each blowing housing is provided with a mounting hole for exposing a charging port component; the mounting hole is communicated to the first mounting cavity; the charging port component is located in the first mounting cavity and is electrically connected to the circuit board; a first limiting member is arranged inside the first mounting cavity; the first limiting member is connected to the blower housing and surrounds a periphery of the charging port component to resist against the charging port component; the mounting hole is provided in the third side of the blowing housing; the blowing housing is further provided with a button hole for mounting a control button; the button hole is communicated to the first mounting cavity; and the button hole is provided in the second side of the blowing housing.

5. The neck fan according to claim 3, further comprising a battery, wherein the battery is electrically connected to the circuit board; a second enclosure wall that is enclosed to form a second mounting cavity is arranged in the accommodating cavity; the second enclosure wall is connected to the blowing housing; the battery is arranged in the second mounting cavity; and the second enclosure wall is arranged around at least three sides of the battery.

6. The neck fan according to claim 5, wherein the first enclosure wall is located between the fan blade group and the second enclosure wall, so that the circuit board is located between the battery and the fan blade group in an extension direction of the blowing housing; the second enclosure wall is arranged around a periphery of the battery; the blowing housing is further provided with at least one second limiting member for resisting against a battery top side and/or a battery bottom side; the battery top side and the battery bottom side are opposite to each other and are respectively adjacent to the periphery of the battery.

7. The neck fan according to claim 5, wherein each blowing housing comprises a first housing located on the second side and a second housing located on the first side; the first housing and the second housing are connected and enclosed to form the blowing housing; the second enclosure wall comprises a first partition plate and a second partition plate which protrude out of and are formed on an inner side wall of the first housing, and a third partition plate and a fourth partition plate which protrude out of and are formed on an inner side wall of the second housing; the first partition plate and the third partition plate resist against each other to form the first enclosure wall; and the second partition plate and the fourth partition plate resist against each other to form the second enclosure wall.

8. The neck fan according to claim 5, wherein the first enclosure wall is provided with a first wiring slot communicated to the first mounting cavity; the second enclosure wall is provided with a second wiring slot communicated to the second mounting cavity; the first wiring slot and the second wiring slot are configured to route a first wire electrically connected to the circuit board and the battery; and the first wiring slot and the second wiring slot are arranged in sequence in an extension direction of the blowing housing.

9. The neck fan according to claim 8, wherein the accommodating cavity has a mounting portion for mounting the fan blade group; the blowing housing further has a first wiring hole, a second wiring hole, and a third wiring slot; the first wiring hole is communicated to the first mounting cavity; the second wiring hole corresponds to and is communicated to the mounting portion; the third wiring slot is arranged on one side of the blowing housing away from the accommodating cavity and is communicated between the first wiring hole and the second wiring hole; and the third wiring slot is configured to accommodate a second wire electrically connected between the fan blade group and the circuit board.

10. The neck fan according to claim 9, wherein the third wiring slot is arranged on the first side and back onto the air inlet; the neck fan further comprises a decorative cover; and the decorative cover is mounted corresponding to the third wiring slot to be connected to the blowing housing, so that a surface of the first side of the blowing housing is smoothly connected to an outer surface of the decorative cover after the mounting.

11. The neck fan according to claim 10, wherein the decorative cover is further provided with a wearing identification; the wearing identification is integrally formed with the decorative cover; the decorative cover is in buckled connection with the blowing housing; the decorative cover comprises a plurality of hooks; the blowing housing comprises a plurality of bayonets; the hooks are clamped to the bayonets; and the plurality of bayonets are respectively adjacent and communicated to the first wiring hole and the second wiring hole.

12. The neck fan according to claim 5, wherein the at least one first air outlet is provided in the fourth side of the blowing housing; the at least one first air outlet comprises a plurality of first air outlet holes; the plurality of first air outlet holes are arranged in sequence in an extension direction of the blowing housing; a portion of the first enclosure wall close to the at least one first air outlet and a portion of the second enclosure wall close to the at least one first air outlet are further enclosed with the blowing housing to form a first air duct; and the fan blade group is configured to suck air through the air inlet and convey the air to the first air outlet through the first air duct.

13. The neck fan according to claim 12, wherein the first enclosure wall and the second enclosure wall are spaced apart, so that the first air duct has an opening; and the neck fan further comprises an air guide portion connected to one end of the second enclosure wall away from the first enclosure wall and gradually facing the first air outlet hole away from the fan blade group.

14. The neck fan according to claim 12, further comprising a neck support connected between the two blowing housings, wherein one of the neck support and each blowing housing is provided with a plug-in hole, and a plug-in column is arranged at a position, corresponding to the plug-in hole, of the other one of the neck support and the blowing housing; and the plug-in column is inserted into the plug-in hole to connect the neck support with the blowing housing.

15. The neck fan according to claim 14, wherein the neck support has a cavity; the cavity penetrates through the neck support in a length direction of the neck support; the cavity is communicated to the accommodating cavities inside the two blowing housings; and the cavity is configured to accommodate a third wire electrically connected to the two blowing housings.

16. The neck fan according to claim 15, wherein a separation plate is arranged inside the neck support; the separation plate is enclosed with a side wall of the neck support to form a second air duct and a threading cavity; the threading cavity is configured to accommodate the third wire; the neck support is provided with at least one second air outlet; the at least one second air outlet is communicated to the second air duct; the fan blade group is further configured to suck air through the air inlet and convey the air to the at least one second air outlet through the second air duct; the at least one second air outlet comprises a plurality of second air outlet holes arranged in the extension direction of the neck support.

17. The neck fan according to claim 1, wherein a length of each first blade is less than a length of the second blade; a curvature of the first blade is greater than a curvature of the second blade; and a height of the first blade in the preset axial direction is less than a height of the second blade in the preset axial direction.

18. The neck fan according to claim 17, wherein the boss is further formed with a motor accommodating slot on one side away from the first centrifugal vane wheel; and the fan blade group further comprises a motor; and the motor is arranged in the motor accommodating slot.

19. The neck fan according to claim 17, wherein a height of the boss in the axial direction is less than the height of the second centrifugal vane wheel in the axial direction; a flow guide portion is arranged at one end of the second centrifugal vane wheel away from the base plate; and a height of one side of the flow guide portion close to the boss is less than a height of one side of the flow guide portion away from the boss.

20. A neck fan, configured to be worn around the neck of a user, and comprising:

a neck fan main body, comprising two blowing main bodies respectively configured to be arranged on two sides of the neck of the user, wherein each blowing main body comprises a blowing housing; the blowing housing forms an accommodating cavity and is provided with at least one air inlet communicated to the accommodating cavity and at least one first air outlet communicated to the accommodating cavity;

fan blade groups, arranged in the accommodating cavities, wherein each fan blade group comprises a boss, an annular base plate arranged on an outer side of the boss, a first centrifugal vane wheel arranged on the boss and comprising a plurality of first blades, and a second centrifugal vane wheel arranged on the base plate and comprising a plurality of second blades; the first centrifugal vane wheel and the second centrifugal vane wheel are arranged on a same side relative to the base plate, and the second centrifugal vane wheel is arranged around a periphery of the first centrifugal vane wheel;

each blowing housing comprises a first side, a second side opposite to the first side, a third side adjacent to the first side and the second side, and a fourth side adjacent to the third side, the first side is an inner side for approaching the neck of a user, and the second side is an outer side arranged in a back-to-back manner with the inner side;

the at least one air inlet is provided in the second side, and corresponds to the first centrifugal vane wheel and the second centrifugal vane wheel; the first side has no air inlet, so that the blowing housing is formed into a single-sided air inlet structure, thereby when the first side approaches the neck of the user, hairs of the user can be avoided from being entangled into the air inlet on the second side; and the first centrifugal vane wheel and the second centrifugal vane wheel are configured to guide air from the air inlet on a single side to the at least one first air outlet for blowing out;

wherein a mounting hole is provided in one of the accommodating cavities, and a charging port component is provided at one of the blowing main bodies, the charging port component comprises a main circuit board and a charging port, the main circuit board is penetrated in the mounting hole in a direction substantially perpendicular to a surface of the one of the blowing main bodies, and the charging port is exposed at the surface of the one of the blowing main bodies; and wherein a first air duct is formed along a lengthwise direction of the one of the blowing main bodies; and the fan blade group is configured to suck air through the air inlet and convey the air to the first air outlet through the first air duct, and the mounting hole does not overlapped with the first air duct.

* * * * *